United States Patent

Dallosta

(12) 
(10) Patent No.: US 6,652,685 B2
(45) Date of Patent: Nov. 25, 2003

(54) METHOD FOR AN INTAGLIO PRESSED BOTANIC ORNAMENT

(76) Inventor: Margaret R. Dallosta, 4039 Baudin St., New Orleans, LA (US) 70119

(*) Notice: Subject to any disclaimer, the term of this patent is extended or adjusted under 35 U.S.C. 154(b) by 247 days.

(21) Appl. No.: 10/003,814

(22) Filed: Oct. 31, 2001

(65) Prior Publication Data

US 2003/0079818 A1 May 1, 2003

(51) Int. Cl.[7] .............. B32B 31/00; A01N 3/00; A01G 5/06
(52) U.S. Cl. .............. 156/63; 156/268; 156/267; 428/17; 428/24
(58) Field of Search .............. 156/57, 59, 63, 156/268, 267; 428/17, 18, 24

(56) References Cited

U.S. PATENT DOCUMENTS

| | | | |
|---|---|---|---|
| 4,279,200 A | * | 7/1981 | Newcomb .............. 428/24 |
| 4,885,037 A | | 12/1989 | Ohkubo |
| 5,354,395 A | | 10/1994 | Fernandez |
| 5,433,803 A | | 7/1995 | Kwan |
| 5,656,343 A | | 8/1997 | Baker |
| 5,662,970 A | | 9/1997 | Noguchi |

* cited by examiner

*Primary Examiner*—Jeff H. Aftergut
(74) *Attorney, Agent, or Firm*—George E. Stanford, Jr.

(57) ABSTRACT

A method for an intaglio botanic ornamental transparency comprising the steps of laminating a botanic assemblage between a transparent, deformable cover layer and a fibrous, opaque backing layer, intaglioing completely all backing layer material facing the botanic assemblage, intaglioing partially a narrow optically diffuse auroral boundary zone of backing layer material circumferential to the periphery of the botanic assemblage, abutting thereto, the backing material residue providing a translucent auroral property to the concomitant transparent cover layer.

19 Claims, 2 Drawing Sheets

Fig. 3
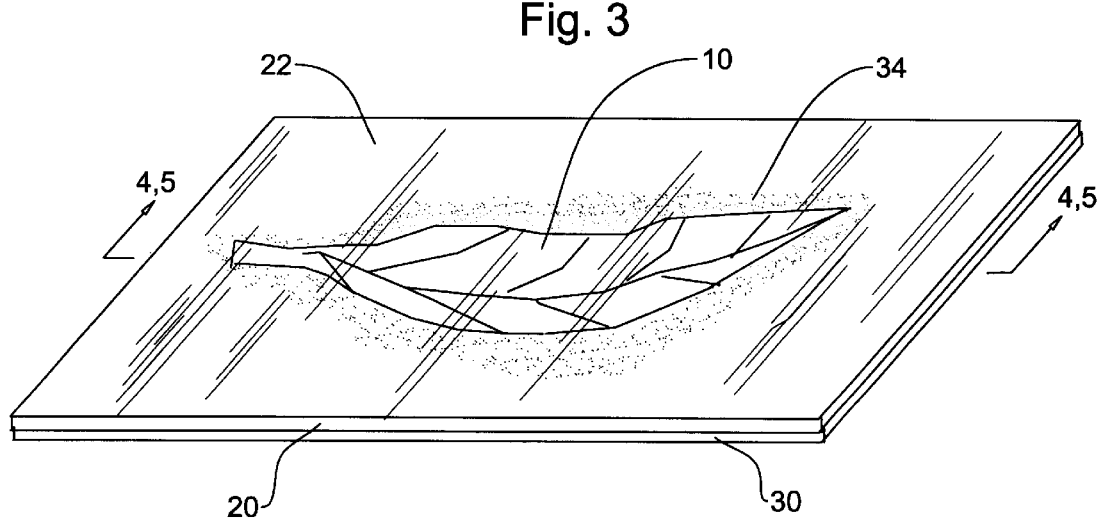
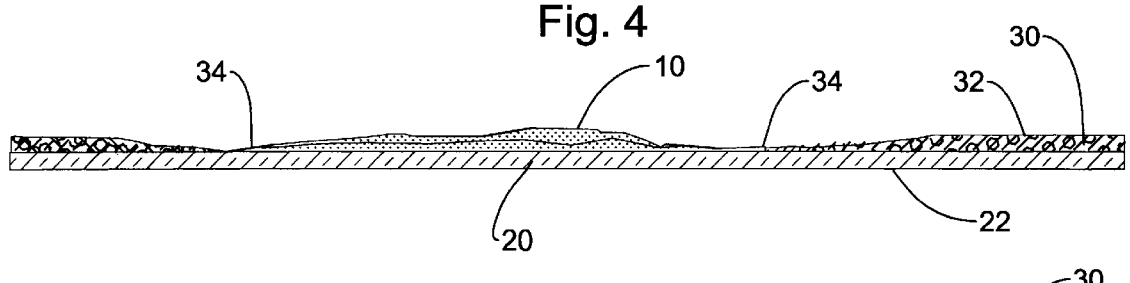
Fig. 4
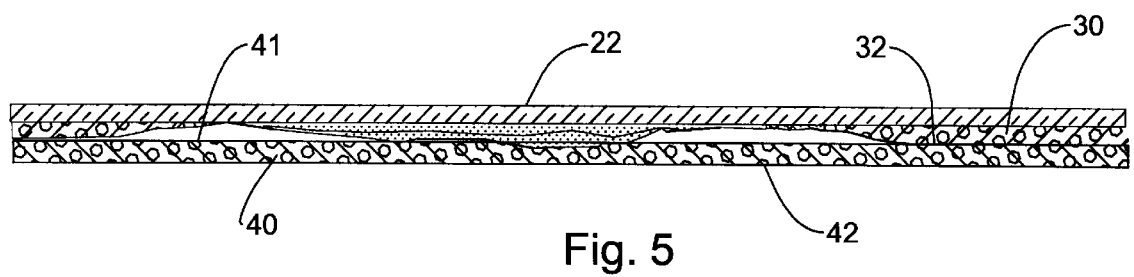
Fig. 5

US 6,652,685 B2

METHOD FOR AN INTAGLIO PRESSED BOTANIC ORNAMENT

BACKGROUND

1. Field of the Invention

The present invention concerns generally a botanic ornamentation. In particular, the present invention is directed to an intaglio, laminated botanic ornamental transparency, generally pictorially viewable from either surface thereof. The botanic ornamentation can include freshly pressed flowers and leaves, and also pressed-and-desiccated flowers and leaves, all suitably arranged as a botanic assemblage.

2. Description of Related Art

The preservation and ornamental presentation of botanic material is a well-established art form. Often, the botanic presentation is a laminate; a desiccated-and-pressed flower is positioned on a backing material and subsequently covered with one or more sealing layers to protect the delicate botanic material. The backing material may include hard, dense materials, such as porcelain, pottery, glass, metal, wood, and synthetic resin; soft, fibrous materials, such as, cloth, leather, and paper; and soft, dense materials, such as films. Alternatively, the pressed-and-desiccated flower is placed between two sealing layers, effectively sealing the flower from air and moisture. U.S. Pat. No. 5,662,970 "SEALED ORNAMENT OF DRIED AND PRESSED FLOWERS" is incorporated herein by reference for purposes of indicating the background of the present invention or illustrating the mature state of the art for preserving and displaying botanic material.

Aforementioned botanic ornamental techniques produce predictable, albeit pedestrian, results. The present invention provides an intaglio method applied to an opaque, fibrous backing layer, producing dramatic, less predictable compositions featuring a bold three-dimensional appearance.

SUMMARY

An object of the present invention is to produce by lamination, a botanic assemblage sandwiched between a deformable, transparent cover layer and a fibrous, opaque backing layer, wherein the botanic assemblage is bonded only to the cover layer and the cover layer is bonded to the backing layer. Another object of the present invention is to provide an intaglio method, which removes completely, all material from the backing layer facing the botanic assemblage. Another object of the present invention is to provide an intaglio method that removes partially the fibrous opaque backing material in a narrow boundary area abutting the periphery of the botanic assemblage, creating thereby in conjunction with the removal of all material from the backing layer facing the botanic assemblage, a translucent ornamental composition comprising the areal extent of the botanic assemblage and a small concomitant optically diffuse auroral zone containing backing material residue abutting thereto. Another object of the present invention is to produce an intaglio laminated botanic ornament viewable from either surface thereof. A further objective of the present invention is to provide an additional layer of material to the layered composition to enhance certain colors of the botanic assemblage and also to enhance the three-dimensional visualization of the ornament.

BRIEF DESCRIPTION OF THE DRAWINGS

FIG. 3 is a perspective view of invention elements upon completion of intaglio of both intaglio backing layer material facing the botanic assemblage and also the intaglio backing layer material in the optically diffuse auroral boundary zone abutting the periphery of the botanic assemblage, according to the present invention. In this view the transparent cover layer is the uppermost layer.

FIG. 4 is an inverted cross-sectional view of FIG. 3, illustrating the pressed botanic assemblage, the planar exterior surface of the cover layer, and the carved exterior surface of the backing layer showing the optically diffuse auroral boundary zone abutting the periphery of the botanic assemblage, according to the present invention.

FIG. 5 is a cross-sectional view of FIG. 3 of an alternate embodiment of the present invention, upon the addition of a depth enhancement and color-control layer facing the backing layer of the present invention. In this view the cover layer is the uppermost layer and the depth enhancement layer is the bottommost layer.

DESCRIPTION OF THE PREFERRED EMBODIMENT

Figure 1:
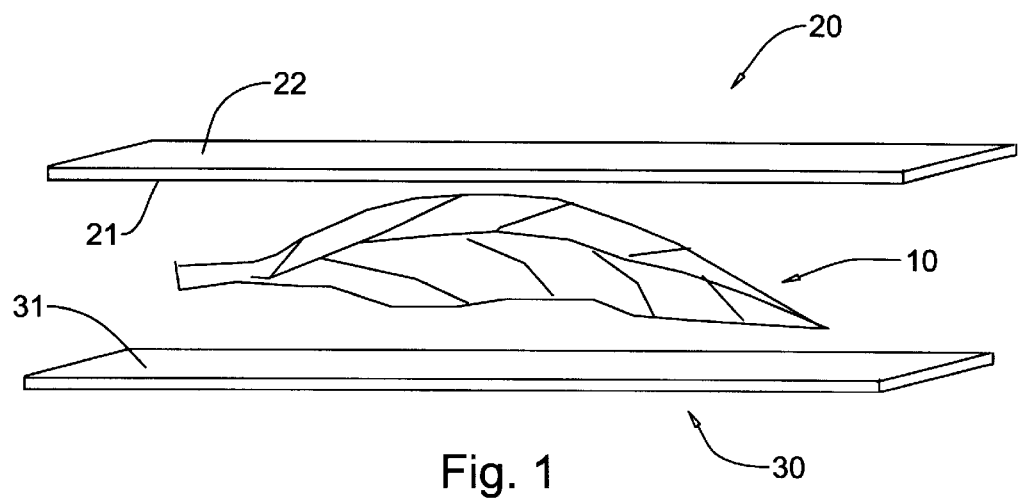
FIG. 1 is a perspective view of the relative position of invention elements prior to lamination, according to the present invention.

The perspective view of FIG. 1 illustrates the initial phase of the intaglio method according to a preferred embodiment of the present invention. Pressed botanic assemblage 10 may include fresh natural flowers and leaves, pressed and desiccated natural flowers and leaves, and artificial flowers and leaves. The objective is to create a dramatic composition, not preserve the fidelity of the assemblage in its natural state; consequently, no special attention is given to color preservation or desiccating the assemblage. Assemblage 10 is positioned between cover layer 20 and backing layer 30. In the preferred embodiment, the cover layer 20 is commercially-available, transparent, deformable sheet plastic, having a cover layer interior adhesive surface 21 and opposite thereto, a cover layer exterior surface 22. In the preferred embodiment, the backing layer is opaque, fibrous construction paper, having a backing layer interior surface 31 and opposite thereto, a backing layer exterior surface 32.

Lamination of assemblage 10, cover layer 20 and backing layer 30 can be performed by any conventional means, hot, cold, iron-on, etc. The critical threefold aspect of the lamination process entails (1) complete fixed bonding between the cover layer interior surface 21 of cover layer 20 with the backing layer interior surface 31, where the two surfaces contact each other; (2) complete fixed bonding between the cover layer interior surface 21 of cover layer 20 with the areal surface of the pressed botanic assemblage 10; and (3) total absence of any adhesive bonding between the areal surface of the pressed botanic assemblage 10 and the backing layer interior surface 31.

In the preferred embodiment, a commercially available laminating machine was employed, IBICO®, featuring a 6 inch wide laminating capability (not shown and not claimed in the present invention).

Figure 2:
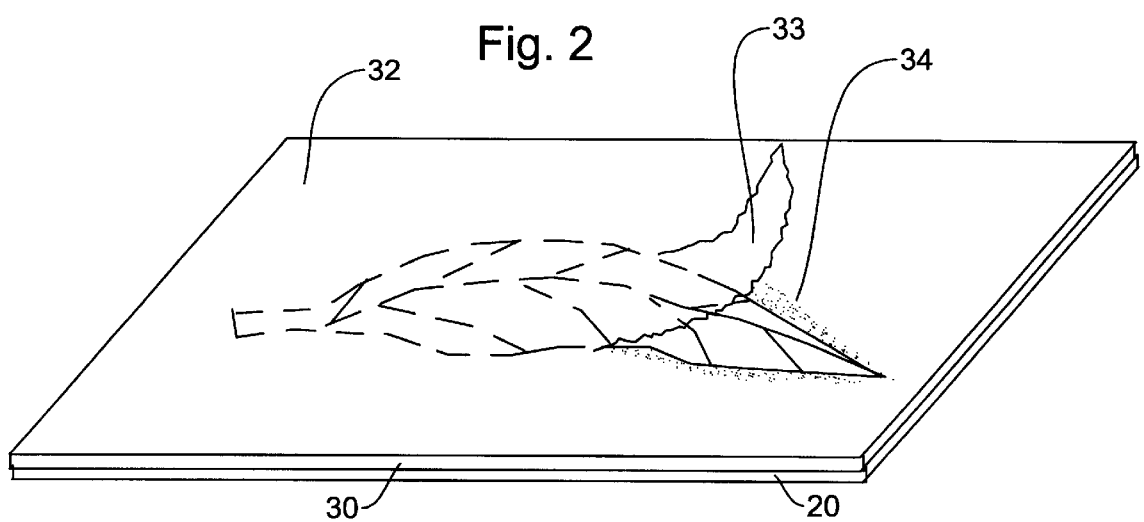
FIG. 2 is a perspective view of invention elements subsequent to lamination and during intaglio of backing layer material facing botanic assemblage, according to the present invention. In this view the backing layer is the uppermost layer.

Following the lamination process, the lamination, as depicted in FIG. 2, was positioned on a light table (not shown and not claimed in the present invention) such that cover layer 20 was closest to the working surface of the light table and the backing layer exterior surface 32 of backing layer 30 was uppermost to the viewer for manual viewing and manipulation. Conceptually, backing layer 30, is partitioned into three zones, first, a fixedly bonded zone wherein backing layer 30 is fixedly and permanently bonded to cover layer 20; second, an intaglio botanic assemblage zone 33, wherein backing layer 30 is in direct contact with botanic assemblage 10, but not bonded thereto; and third, an intaglio optically diffuse auroral zone 34, wherein portions of backing layer 30 are temporarily and partially bonded to cover layer 20. Auroral zone 34 is a generally narrow parallel band adjacent the perimeter of botanic assemblage 10.

The next step is complete removal by intaglio of all backing layer material 30 existing in intaglio botanic assemblage zone 33. Viewing the intaglio of assemblage 10 with the light table back lighting expeditiously reveals visual composition of assemblage 10. Next partial removal by intaglio of portions of backing layer material 30 existing in intaglio optically diffuse auroral zone 34 is performed around the periphery of assemblage 10. The width of auroral zone 34 in the preferred embodiment is generally less than 10 mm.

The intaglio optically diffuse auroral zone 34 occupies a portion of the backing layer 30 that was completely bonded to cover layer 20; consequently, there is some fibrous backing layer material residue remaining on the cover layer interior surface 21, when intaglio removes almost all the backing layer material. Intaglio creates an optically diffuse transmissive gradient in zone 34, extending from virtually 100% light transmission at the zone boundary with the periphery of assemblage 10 to 0% transmission at the outer edge of the zone 34, bordering the remaining portion of backing layer 30. The resultant effect is a gradient translucence encompassing the periphery of assemblage 10. The resulting dramatically vivid effect upon the appearance of assemblage 10 is unexpected; the diffuse lighting effect surrounding botanic assemblage 10 is unique and suggests the auroral morning light of dawn shining through the botanic assemblage.

FIG. 3 illustrates the finished product of the preferred embodiment of the present invention, pressed botanic assemblage 10, encompassed by optically diffuse auroral boundary zone 34 of backing layer 30, and presented underneath the cover layer exterior surface 22, of transparent cover layer 20.

FIG. 4, an inverted, cross-sectional view of FIG. 3, illustrates the intaglio process, revealing the contours of botanic assemblage 10 and the carved optically diffuse auroral boundary zone 34. Also depicted is the cross-section of cover layer 20, and its cover layer exterior surface 22, and the carved cross-section of backing layer 30, and its backing layer exterior surface 32.

FIG. 5 depicts an alternative embodiment of the present invention that additionally entails placing an enhancement layer 40, with enhancement layer exterior surface 42 and enhancement layer interior surface 41, against backing layer 30, such that backing layer exterior surface 32 and enhancement layer interior surface 41 of enhancement layer 40 are in direct contact with each other.

EXAMPLE ONE

This first example demonstrates how the present invention has been manually practiced using: (1) an assembled collection of pressed flowers and leaves; (2) a commercially available laminating machine with a flat cardboard workpiece cover, i.e. an IBICO® laminating machine, model ISG 3215 DSD, featuring a 6 inch wide laminating capacity; (3) a roll of commercially available, medium weight, laminating film, having a thermally-activated adhesive coating on one side; (4) two pieces of opaque, fibrous construction paper; each of a different color; the solid color existing all the way through the paper; and (5) a pair of scissors, featuring sharp points.

One of the two pieces of colored construction paper was chosen to be the backing layer; the remaining piece of construction paper was designated the enhancement layer. The backing layer was placed upon a flat work surface; thereupon, some of the pressed flowers and leaves were placed decoratively on the backing layer, forming a botanic assemblage. Next, a piece of the laminating film was cut and trimmed to correspond to the size of the backing layer. The sized laminating film was designated the cover layer. The cover layer was carefully placed on the backing layer, the thermally-activated adhesive surface facing toward the botanic assemblage, totally covering the backing layer surface holding the botanic assemblage. The combination of the cover layer, botanic assemblage, and the backing layer was designated the laminate workpiece.

After the laminating machine was been turned on and adjusted to function at an operating temperature of 160 degrees Centigrade, the flat cardboard workpiece cover was then placed over the cover sheet and the cover and workpiece were processed through the laminating machine. The cardboard workpiece cover was used to prevent direct contact between the laminating film cover layer and the heating elements of the laminating machine. After the first pass through the laminating machine, the cardboard cover was no longer needed and was removed from the laminate workpiece. The laminate workpiece was flipped over, reversing the cover layer and backing layer surfaces in respect to the laminating machine, exposing the backing layer to proximate contact with heated elements of the laminating machine, and thereupon processed a second time through the laminating machine. The objective here was to assure all air bubbles were removed from areas where there was intended direct contact between the cover layer and backing layer and also to assure the two layers were thoroughly and fixedly bonded with the thermally-activated adhesive present on the cover layer.

After the second, and final, pass through the laminating machine, the laminate workpiece was examined to determine where best to begin intaglio of the backing layer. Upon determination of the starting point for the intaglio, the laminate workpiece was held in one hand, the index finger of that hand pressing on the intaglio starting point and the opposing thumb pressed upon the backing layer. Taking the scissor in the opposite hand, the point of the scissor was carefully pressed into the backing layer, piercing the backing layer while avoiding any disturbance of the botanic assemblage immediately thereunder.

The workpiece was then placed, backing layer upwards, on the light table for easier viewing of the intaglio process. Beginning at the starting point piercing, manual intaglio proceeded with careful incisive carving away of the backing layer, slowly removing portions of the backing layer from the laminate workpiece in the immediate vicinity of the botanic assemblage, not only from the zone directly opposite the botanic assemblage, but additionally in a narrow auroral boundary zone proximate to the periphery of the botanic assemblage, where the backing layer and the cover layer were partially bonded to each other. In the auroral boundary zone surrounding the botanic assemblage, conditions existed wherein there was either no bonding between cover layer and backing layer (i.e. air pocket or bubble) or only partial bonding as a result of incomplete partial adhesion between the layers. This partial bonding effect is due to the inability or inconsistency of the thermally deformable cover layer to deform sufficiently to produce an abrupt demarcation between the elemental laminate composed only of the backing layer and the cover layer, and the assemblage laminate composed of the backing layer, the botanic assemblage, and the cover layer. As a result of that condition, intaglio produced either a transparent or translucent property of the cover layer when light passed there through, producing a diffuse auroral condition surrounding the botanic assemblage.

Viewed from either side, the laminate workpiece presented a scene of the botanic assemblage, surrounded by a narrow auroral zone, which in turn, was surrounded by the backing layer. Upon visually deciding which side of the laminate workpiece presented the better view, the second, enhancement layer was fixedly placed behind the laminate workpiece, providing two contrasting colors to dramatize vividly the arrangement of the botanic assemblage.

EXAMPLE TWO

Similar to the first example, this second example, with an important exception, demonstrates how the present invention was practiced. The exception was the material used for the backing layer. In example two, the backing layer was carbon paper. As in the first example, a decorative arrangement of pressed natural flowers and leaves was placed on the backing layer, in this case, the carbon side of the carbon paper, creating a botanic assemblage on a very dark backing. The cover layer, cut from the roll of medium weight laminating film with a thermally-activated adhesive coating on one side, was then placed over the botanic assemblage and the laminate workpiece was processed through the laminating machine.

Subsequent intaglio of the carbon paper backing layer produced a very clean incised carving over the botanic assemblage and a narrow 3 mm wide auroral boundary zone proximate to the botanic assemblage. In this special case, the auroral boundary zone was totally transparent, producing a silhouette appearance of the botanic assemblage, surrounded by the transparent auroral boundary zone and the very dark carbon paper backing layer.

Although only a few exemplary embodiments of the invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A method of making an intaglio pressed botanic ornamental transparency, comprising the following steps:
   arranging a pressed botanic assemblage on a backing layer;
   positioning a cover layer upon said pressed botanic assemblage, covering thereby both said assemblage and said backing layer;
   laminating said cover layer to said backing layer with said pressed botanic assemblage sandwiched there in between; and
   intaglioing a portion of said backing layer, revealing thereby both said undisturbed botanic assemblage and an optically diffuse auroral boundary zone thereof.

2. A method of making an intaglio pressed botanic ornamental transparency, as recited in claim 1, wherein said botanic assemblage is selected from a group consisting of freshly pressed natural flowers and natural leaves; pressed-and-desiccated natural flowers and natural leaves; and artificial flowers and artificial leaves.

3. A method of making an intaglio pressed botanic ornament, as recited in claim 2, wherein said backing layer is a material selected from a group consisting of paper, carbon paper, leather, foil, metal, cloth, and wood.

4. A method of making an intaglio pressed botanic ornament, as recited in claim 3, wherein said cover layer is a material selected from a group consisting of plastic, plastic film, and glass.

5. A method of making an intaglio pressed botanic ornament, as recited in claim 4, wherein said boundary zone resulting from intaglio exhibits an optical transmittance gradient extending from maximum transmittance at the inner edge of said boundary zone, defined by the periphery of said botanic assemblage to minimum transmittance at the outer edge of said boundary zone.

6. A method of making an intaglio pressed botanic ornament, as recited in claim 5, wherein intaglio is performed by a method selected from the group consisting of hand-guided non-powered tool, hand-guided power tool, machine-guided tool, and computer-guided tool.

7. A method of making an intaglio pressed botanic ornament, as recited in claim 6, further comprising:
   positioning fixedly a depth enhancement and color control layer against the backing layer exterior surface of said backing layer.

8. A method of making an intaglio pressed botanic ornament, as recited in claim 7, wherein said depth enhancement and color control layer is a material selected from a group consisting of paper, carbon paper, leather, foil, metal, cloth, and wood.

9. A method of making an intaglio pressed botanic ornamental transparency, comprising the following steps:
   laminating a pressed botanic assemblage between a backing layer and a cover layer; and
   intaglioing a portion of said backing layer, revealing both said undisturbed botanic assemblage and a boundary zone thereof.

10. A method of making an intaglio pressed botanic ornamental transparency, as recited in claim 9, wherein said botanic assemblage is selected from a group consisting of freshly pressed natural flowers and natural leaves; pressed-and-desiccated natural flowers and natural leaves; and artificial flowers and artificial leaves.

11. A method of making an intaglio pressed botanic ornament, as recited in claim 10, wherein said backing layer is a material selected from a group consisting of paper, carbon paper, leather, foil, cloth, and wood.

12. A method of making an intaglio pressed botanic ornament, as recited in claim 11, wherein said cover layer is a material selected from a group consisting of plastic, plastic film, and glass.

13. A method of making an intaglio pressed botanic ornament, as recited in claim 12, wherein said boundary zone resulting from intaglio exhibits an optical transmittance gradient extending from maximum transmittance at the inner edge of said boundary zone, defined by the periphery of said botanic assemblage to minimum transmittance at the outer edge of said boundary zone.

14. A method of making an intaglio pressed botanic ornament, as recited in claim 13, wherein intaglio is performed by a method selected from the group consisting of hand-guided non-powered tool, hand-guided power tool, machine-guided tool, and computer-guided tool.

15. A method of making an intaglio pressed botanic ornament, as recited in claim 14, further comprising:

positioning fixedly a depth enhancement and color control layer against the backing layer exterior surface of said backing layer.

16. A method of making an intaglio pressed botanic ornament, as recited in claim 15, wherein said depth enhancement and color control layer is a material selected from a group consisting of paper, carbon paper, leather, foil, cloth, and wood.

17. A method of making an intaglio pressed botanic ornamental transparency, comprising the following steps:

arranging a pressed botanic assemblage on a backing layer, said assemblage having a collection of pressed natural flowers and natural leaves, said backing layer composed of opaque, fibrous paper;

positioning a transparent, plastic, thermally deformable cover layer, said cover layer coated with thermally activated adhesive on one side thereof, upon said pressed botanic assemblage, covering both said assemblage and said backing layer;

laminating thermally said cover layer to said backing layer with said pressed botanic assemblage sandwiched there in between; and intaglioing a portion of said backing layer, creating and revealing thereby both said undisturbed botanic assemblage and an optically diffuse auroral boundary zone thereof, said auroral boundary zone having an optical transmittance gradient extending from maximum transmittance at the inner edge of said boundary zone abutting periphery of said assemblage to minimum optical transmittance at the outer edge of said auroral boundary zone.

18. A method of making an intaglio pressed botanic ornament, as recited in claim 17, further comprising:

positioning fixedly a depth enhancement and color control layer against the backing layer exterior surface of said backing layer.

19. A method of making an intaglio pressed botanic ornament, as recited in claim 18, wherein said depth enhancement and color control layer is a material selected from a group consisting of paper, carbon paper, leather, foil, metal, cloth, and wood.

* * * * *